US012747159B2

(12) United States Patent
Bode et al.

(10) Patent No.: US 12,747,159 B2
(45) Date of Patent: Sep. 29, 2026

(54) CIRCULAR CARBON PROCESS

(71) Applicant: BASF SE, Ludwigshafen Am Rhein (DE)

(72) Inventors: Andreas Bode, Ludwigshafen (DE); Dieter Flick, Ludwigshafen (DE); Andreas Spiegel, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 730 days.

(21) Appl. No.: 17/999,912

(22) PCT Filed: May 26, 2021

(86) PCT No.: PCT/EP2021/064090
§ 371 (c)(1),
(2) Date: Nov. 25, 2022

(87) PCT Pub. No.: WO2021/239831
PCT Pub. Date: Dec. 2, 2021

(65) Prior Publication Data

US 2023/0227316 A1 Jul. 20, 2023

(30) Foreign Application Priority Data

May 27, 2020 (EP) .................................... 20176799
Jun. 8, 2020 (EP) .................................... 20178657

(51) Int. Cl.
*C01B 32/40* (2017.01)
*B01J 6/00* (2006.01)
(Continued)

(52) U.S. Cl.
CPC ............... *C01B 32/40* (2017.08); *B01J 6/008* (2013.01); *B01J 19/245* (2013.01); *C01B 3/24* (2013.01);
(Continued)

(58) Field of Classification Search
CPC ....... C01B 32/40; C01B 32/05; C01B 32/942; C01B 3/24; B01J 6/008; C22B 5/10
See application file for complete search history.

(56) References Cited

U.S. PATENT DOCUMENTS 4,242,105 A 12/1980 Frost
5,213,770 A 5/1993 Noyes
(Continued)

FOREIGN PATENT DOCUMENTS

CN 101563439 A 10/2009
CN 102597182 A 7/2012
(Continued)

OTHER PUBLICATIONS

Abbas, et al., "Hydrogen production by methane decomposition: a review", International journal of hydrogen energy, vol. 35, Issue 3, Feb. 2010, pp. 1160-1190.
(Continued)

*Primary Examiner* — Anthony J Zimmer
*Assistant Examiner* — Annette Phan
(74) *Attorney, Agent, or Firm* — Grüneberg Global IP, PLLC

(57) ABSTRACT

A circular carbon process involves: a) reacting hydrogen and carbon monoxide to produce methane and water, b) decomposing methane into carbon and hydrogen, and c) using carbon as reducing agent and/or using carbon in a carbon-containing material as reducing agent, in a chemical process to produce carbon monoxide and a reduced substance. The methane produced in a) is used in b), the carbon produced in b) is used in c), and carbon monoxide produced in c) is used in a).

12 Claims, 1 Drawing Sheet

(51) Int. Cl.

| | |
|---|---|
| ***B01J 19/24*** | (2006.01) |
| ***C01B 3/24*** | (2006.01) |
| ***C01B 3/34*** | (2006.01) |
| ***C01B 25/02*** | (2006.01) |
| ***C01B 32/05*** | (2017.01) |
| ***C01B 32/942*** | (2017.01) |
| ***C01B 32/97*** | (2017.01) |
| ***C01B 33/025*** | (2006.01) |
| ***C01G 45/02*** | (2025.01) |
| ***C07C 1/04*** | (2006.01) |
| ***C22B 5/10*** | (2006.01) |
| ***C22B 25/02*** | (2006.01) |
| ***C22B 34/32*** | (2006.01) |

(52) U.S. Cl.

CPC ................ *C01B 3/34* (2013.01); *C01B 25/02* (2013.01); *C01B 32/05* (2017.08); *C01B 32/942* (2017.08); *C01B 32/97* (2017.08); *C01B 33/025* (2013.01); *C01G 45/02* (2013.01); *C07C 1/0485* (2013.01); *C22B 5/10* (2013.01); *C22B 25/02* (2013.01); *C22B 34/32* (2013.01); *C01B 2203/0233* (2013.01); *C01B 2203/0272* (2013.01); *C01B 2203/062* (2013.01)

(56) References Cited

U.S. PATENT DOCUMENTS

| | | | | |
|---|---|---|---|---|
| 5,232,951 | A * | 8/1993 | Pfingstl | C01B 32/97 518/702 |
| 5,316,565 | A | 5/1994 | Kibby | |
| 5,527,518 | A * | 6/1996 | Lynum | C09C 1/487 423/449.1 |
| 6,551,489 | B2 | 4/2003 | D'Astolfo, Jr. et al. | |
| 8,236,274 | B2 * | 8/2012 | Quitmann | C09C 1/52 106/478 |
| 8,568,512 | B2 | 10/2013 | Siegel et al. | |
| 11,712,652 | B2 * | 8/2023 | Spiteri | C01B 3/24 423/449.1 |
| 2011/0123428 | A1 | 5/2011 | Liu et al. | |
| 2017/0204335 | A1 * | 7/2017 | Ravikumar | C01B 3/38 |
| 2018/0319661 | A1 * | 11/2018 | Isobe | C07C 1/12 |
| 2019/0218094 | A1 | 7/2019 | Godal | |

FOREIGN PATENT DOCUMENTS

| | | | |
|---|---|---|---|
| CN | 106315584 | A | 1/2017 |
| CN | 106883084 | A | 6/2017 |
| CN | 110022964 | A | 7/2019 |
| EP | 2682450 | A2 | 1/2014 |
| EP | 3548565 | A1 | 10/2019 |
| GB | 2449234 | A | 11/2008 |
| JP | S60-190726 | A | 9/1985 |
| JP | H07-504707 | A | 5/1995 |
| JP | 2008-038153 | A | 2/2008 |
| JP | 2011-529840 | A | 12/2011 |
| JP | 2015196619 | A * | 11/2015 |
| JP | 2017-197399 | A | 11/2017 |
| JP | 2019-523209 | A | 8/2019 |
| KR | 20110013968 | A | 2/2011 |
| KR | 20180117951 | A | 10/2018 |
| KR | 20200039499 | A | 4/2020 |
| WO | WO-2018/069503 | A2 | 4/2018 |
| WO | WO-2018/099709 | A1 | 6/2018 |
| WO | WO-2020/016186 | A1 | 1/2020 |

OTHER PUBLICATIONS

European Search Report for EP Patent Application No. 20176799.3, Issued on Nov. 19, 2020, 3 pages.

Fulcheri, et al., "From methane to hydrogen, carbon black and water", International Journal of Hydrogen Energy, vol. 20, Issue 3, Mar. 1995, pp. 197-202.

International Search Report for PCT Patent Application No. PCT/EP2021/064090, Issued on Jul. 13, 2021, 4 pages.

Müller, et al., "Energy Storage by CO2 Methanization and Energy Carrying Compounds: A Thermodynamic Comparison", Chemie Ingenieur Technik, vol. 83, Issue 11, Oct. 11, 2011, pp. 2002-2013.

Muradov, et al., "Green path from fossil-based to hydrogen economy: an overview of carbon-neutral technologies", International journal of hydrogen energy, vol. 33, Issue 23, Dec. 2008, pp. 6804-6839.

N. Z. Muradov, "How to produce hydrogen from fossil fuels without CO2 emission", International Journal of Hydrogen Energy, vol. 18, Issue 3, Mar. 1993, pp. 211-215.

Rönsch, et al., "Review on methanation-From fundamentals to current projects", Fuel, vol. 166, Feb. 15, 2016, pp. 276-296.

International Preliminary Report on Patentability for PCT Patent Application No. PCT/EP2021/064090, Issued on Dec. 8, 2022, 8 pages.

Written Opinion for PCT Patent Application No. PCT/EP2021/064090, Issued on Jul. 13, 2021, 6 pages.

* cited by examiner

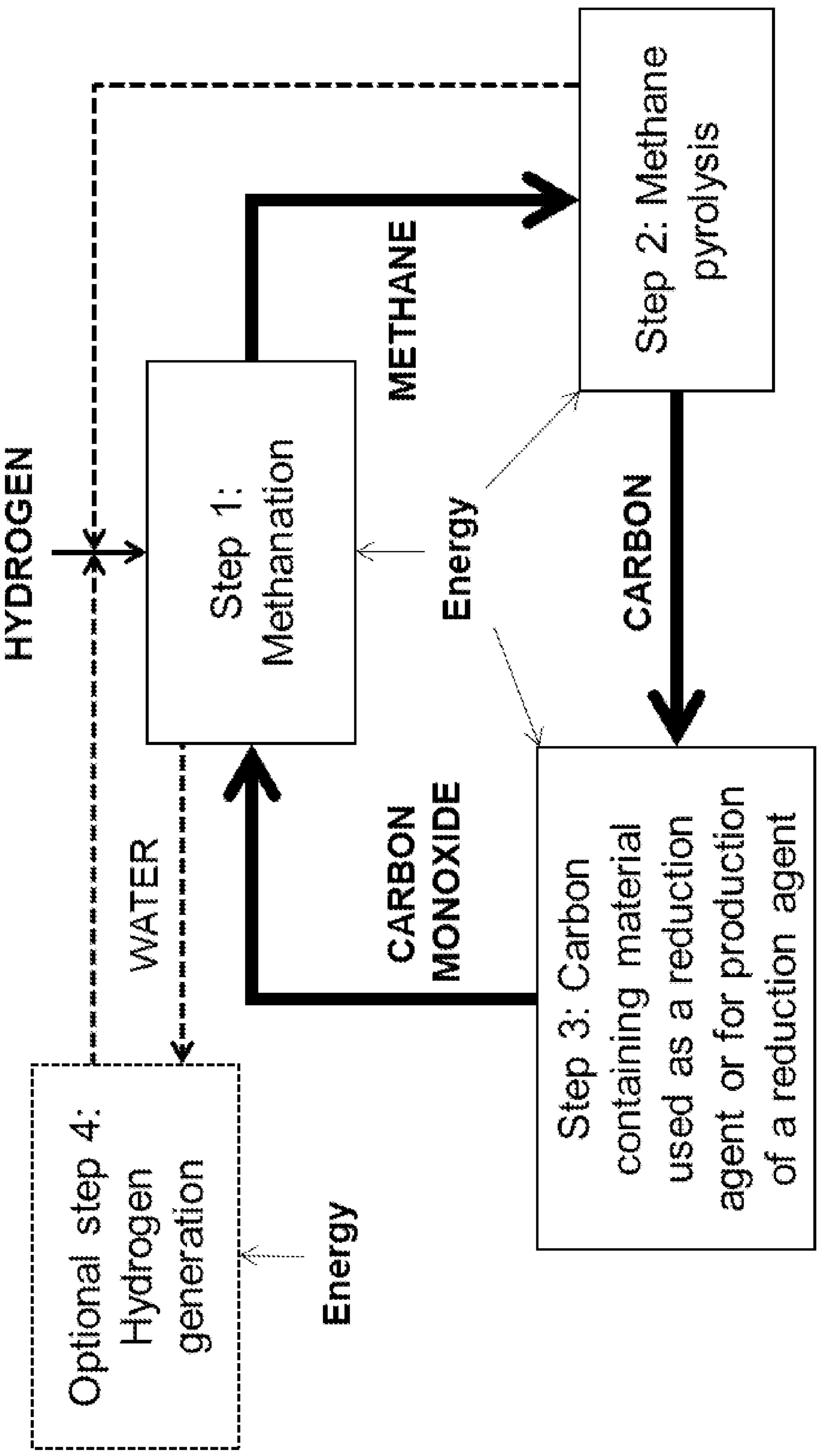
Step 1: Methanation
Step 2: Methane pyrolysis
Step 3: Carbon containing material used as a reduction agent or for production of a reduction agent
Optional step 4: Hydrogen generation
HYDROGEN
METHANE
CARBON
CARBON MONOXIDE
WATER
Energy
Energy

CIRCULAR CARBON PROCESS

CROSS-REFERENCE TO RELATED APPLICATIONS

This application is the National Stage entry under § 371 of International Application No. PCT/EP2021/064090, filed on May 26, 2021, and which claims the benefit of priority to European Application No. 20176799.3, filed on May 27, 2020, and priority to European Application No. 20178657.1, filed on Jun. 8, 2020. The content of each of these applications is hereby incorporated by reference in its entirety.

BACKGROUND OF THE INVENTION

Field of the Invention

The present invention relates to a process for a circular carbon process comprising a first step wherein hydrogen and carbon monoxide are reacted to produce methane and water, a second step wherein methane is decomposed into carbon and hydrogen, a third step wherein carbon is used as a reducing agent and/or carbon is used in a carbon-containing material as reducing agent in a chemical process to produce carbon monoxide and a reduced substance, and optionally a fourth step wherein hydrogen is produced, whereas, the methane produced in the first step is used in the second step, whereas carbon produced in the second step is used in the third step and whereas carbon monoxide produced in the third step is used in the first step. In addition, the present invention relates to a joint plant for circular carbon process comprising: a plant using carbon as reduction agent in a chemical reactor including a CO separation and conditioning downstream of the chemical reactor, a methanation plant downstream producing methane and water, a pyrolysis plant downstream of the methanation plant decomposing methane to solid carbon and hydrogen.

Description of Related Art

The increasing concentration of carbon dioxide in the atmosphere has been linked to current and future global warming. Various methods have been put forward to reduce the atmospheric concentration of carbon dioxide, either by reducing the carbon dioxide emissions or by sequestering the carbon dioxide.

Currently, CO2 emissions are regulated by CO2 certificates e.g. in the European Union, which will most likely become more expensive year after year. It is under discussion whether CO2 emissions could be banned in the foreseeable future.

In recent years, industries whose CO2 emissions are based on using carbon-containing material as an energy source started to reduce or even completely eliminate CO2 emissions with manageable effort, e.g. via electrification and the shift from oil and natural gas to hydrogen. It is expected that the need of hydrogen and renewable energy increases rapidly.

However, carbon is a typical reducing agent and is used in many industrial processes, mainly but not exclusively for metals. Examples (J. House: inorganic Chemistry, 2013 Academic Internet Publishers, M. Bertau et al: Industrielle Anorganische Chemie, 2013 Wiley-VCH) are the production of:

calcium carbide $CaO+3C \rightarrow CaC_2+CO$ silicon carbide $SiO_2+3C \rightarrow SiC+2CO$ silicon $SiO_2+2C \rightarrow Si+2CO$ tin $SnO_2+2C \rightarrow Sn+2CO$ chromium $Cr_2O_3+3C \rightarrow 2Cr+3CO$ manganese oxide $MnO_2+C \rightarrow MnO+CO$ phosphorus $2Ca_3(PO_4)_2+6SiO_2+10C \rightarrow P_4+10CO+6CaSiO_3$.

Carbon monoxide can be used as raw material either pure or mixed with hydrogen as synthesis gas for many different processes in the chemical industry, but it is often used energetically in combustion processes $2CO+O_2 \rightarrow CO_2$ for electricity and steam production. If CO is oxidized, CO2 will be the main product. CO2 is only used in very few processes as a raw material e.g. for urea production, but in most cases will be emitted to atmosphere.

Industries that use carbon-containing material as a reducing agent as described in the examples, cannot stop their CO2 emission via electrification since carbon is necessary for production of the target product. These industries need an alternative reducing agent or alternative methods for emission reduction like Carbon Capture and Utilization (CCU) or Carbon Capture and Storage (CCS) or utilization of biomass and waste.

Recently it was disclosed in WO2020/016186 that pyrolytic carbon can be used as blend material in carbon-based aluminum anodes for the reduction of alumina oxide to aluminum. The production of aluminum is carried out in electrolytic cells or pots (known as Hall-Héroult process). Electrolysis of Al2O3 occurs in a molten bath of cryolite layered between the carbon electrodes and the molten metal. Aluminum ions within Al2O3 react with the carbon anode producing reduced molten aluminum and carbon dioxide. The carbon used for the anodes is typically petroleum coke in addition to recycled anode butts and coal tar pitch binder.

Although the climate discussion and studies to achieve CO2 neutral production started more than 20 years ago, only a few studies on alternatives to carbon-based anodes has been disclosed yet. For example, U.S. Pat. No. 6,551,489 discloses an inert anode assembly replacing the consumable carbon anode.

WO 2018/099709 discloses a CO2 cycle including the following steps (i) isolating CO2 from atmospheric air or flue gas, (ii) converting CO2 and H2 into hydrocarbons ($CO_2+4H_2 \rightarrow CH_4+2H_2O$), (iii) cracking these hydrocarbons and (iv) using the carbon in metallurgy as carburizer, as reducing agent, as filler, as pigments etc. and generating CO2 during these applications. Half of the needed hydrogen for the methanation in step (ii) can be provided by recycling of hydrogen from the cracking process of step (iii), the other half can be supplied by electrolysis of water using electricity.

A recycle of oxygen is known from the discussion of manned missions to the Mars.

U.S. Pat. No. 5,213,770 and US 2018/319661 disclose a method for oxygen recovery from carbon dioxide exhaled combining the following process steps: (i) a reduction of CO2 with hydrogen to methane and water (Sabatier Process, Methanation), (ii) a pyrolysis of methane to solid carbon and hydrogen and (iii) a water electrolysis to get hydrogen and the needed oxygen, whereas hydrogen of the process step (ii) and (iii) are used for the reduction step (i) and exhaled carbon dioxide is used as starting material in step (i).

In addition, the conversion of carbon dioxide to solid carbon was discussed in connection with the question of $CO_2$ sequestration. GB 2 449 234 discloses a method of sequestration of atmospheric carbon dioxide via the combined process of Sabatier and methane pyrolysis analogously to U.S. Pat. No. 5,213,770 and US 2018/319661. The solid carbon can be sequestrated easily compared to an $CO_2$ capture and sequestration.

Facing the $CO_2$ targets and the rapid need for hydrogen and electricity, carbon cycles are needed that are efficient in hydrogen and energy use, especially for industries based on carbon as reducing agents.

SUMMARY OF THE INVENTION

The present invention is thus based on the task of prevention of $CO_2$ emissions despite the use of carbon-based material as reducing agent in a chemical process. Instead of using the resulting carbon monoxide in combustion processes for electricity and steam production energetically, carbon monoxide shall be used as raw material and thus shall be kept in a circular carbon process. In addition, the carbon cycle shall be hydrogen, energy and heat transfer efficient. In addition, the pressure drop shall be low, especially in the methanation step. In addition, the carbon shall remain in the carbon cycle without any carbon oxide emissions. In addition, the carbon cycle shall allow dynamic operation.

Surprisingly, a method for a circular carbon process was found comprising

- a first step wherein hydrogen and carbon monoxide are reacted to produce methane and water ($CO+3H_2 \rightarrow CH_4+H_2O$),
- a second step wherein methane is decomposed into carbon and hydrogen ($CH_4 \rightarrow 2H_2+C$),
- a third step wherein carbon is used as reducing agent and/or carbon is used in a carbon-containing material as reducing agent in a chemical process to produce carbon monoxide and a reduced substance, whereas the methane produced in the first step is used in the second step, whereas the carbon produced in the second step is used in the third step and carbon monoxide produced in the third step is used in the first step.

BRIEF DESCRIPTION OF THE DRAWING

The FIGURE shows a schematic diagram of the circular carbon process according to the invention.

DETAILED DESCRIPTION OF THE INVENTION

The circular carbon process offers multiple options for adaptations to the concrete process using the carbon containing material (third step), to site and economic conditions. The options are for example:

- reaction heat from the exothermic methanation reaction (first step) or excess heat from the methane pyrolysis process (second step) can be used for CO separation or purification in the third step or externally of the circular carbon process
- hydrogen from methane pyrolysis (second step) can be used in the methanation (first step)
- additional hydrogen can be produced in an additional fourth step
- water from methanation (first step) can be used for hydrogen generation in the additional fourth step
- water electrolysis or steam reforming of methane can be used for hydrogen generation
- another hydrogen production plant can supply hydrogen to the methanation
- streams of $H_2$, $CH_4$, CO, $CO_2$, and/or C can be introduced into the cycle at different points like $H_2$ in the first and/or third steps, $CH_4$ and other light hydrocarbons in the second and/or third steps, CO/$CO_2$ in the first step, CO in the third step
- analogously to introduction of the streams of $H_2$, $CH_4$, CO, $CO_2$, and/or C into the cycle, the streams can be extracted from the cycle to supply external demand and/or for storage of carbon.

All steps are involving chemical reactions and additional processing with their respective energy input or output of electricity and heat. Overall, the circular carbon process will need energy input to compensate for the chemical reactions and the irreversibility of the processes. To achieve the target of prevention of $CO_2$ emissions, the energy demand of the circular process is preferably to be supplied from renewable sources or nuclear power generating electricity or heat near zero or completely without $CO_2$ emissions. Preferred energy source is electricity with a carbon footprint <250 kg/MWh, more preferred <100 kg/MWh. The circular carbon process is depicted schematically in the FIGURE.

The circular carbon process enables to avoid $CO_2$ emissions, but also offers the option to extract carbon from the cycle. This extracted carbon can be stored for long-term. Carbon extraction and storage is relevant to compensate for carbon and/or carbon containing materials introduced into the cycle being or generating $CO_2$. The $CO_2$ can be emitted and/or can be processed in steps 1 and 2, whereas the carbon generated in step 2 can then be extracted and stored. By this method, the carbon balance for the overall cycle can be maintained. As well, $CO_2$ emissions can be compensated which stem from electricity generation and/or from upstream production of other raw materials used in steps of the cycle.

The following describes the steps of the circular carbon process, preferred requirements for energy supply and the conditioning and purification of streams flowing from one step to the other.

The energy demand of the circular carbon process depends on the process steps combined and their design. Basically, the processes for reducing salts in the third step—see examples above—have a high energy demand as endothermic reactions. The conversion of carbon monoxide and hydrogen in the first step is exothermic, methane pyrolysis in the second step is endothermic.

The circular processing of carbon is always accompanied by losses due to not perfect process realization, so that carbon losses are preferably compensated. This can be done by adding streams of carbon containing substances like C, $CO_2$, CO, or $CH_4$ into the cycle.

Circular processing requires conditioning and purification of material streams since chemical components can accumulate in the cycle of the circulated materials. This is a well-known requirement in chemical engineering, where any recycle stream is preferably purified and conditioned so that effects of the accumulation of substances within this recycle stream can be tolerated by subsequent processing steps regarding product quality and process performance.

In addition, the overall optimum of the circular process determines the operating conditions for the separate steps, so that the purification and conditioning requirements of material stream can be different from the requirements when operating the steps separately.

Purification and conditioning before the first step:

The preferred methanation involves a catalytic reaction using nickel on alumina catalysts at 5 to 60 bar, preferably 10 to 45 bar and 200 to 550° C. The raw material streams of carbon monoxide optionally including minor amounts of carbon dioxide and hydrogen are preferably purified and conditioned to meet the conditions necessary for the first step to operate safely and with high performance.

Carbon monoxide and hydrogen should contain as low amounts as possible of catalyst contaminants like e.g. sulfur containing compounds or catalyst poisons like chlorine. The optimum level of contaminants depends on catalyst and process design of the methanation since purification of feed streams generates cost but improves catalyst performance and lifetime. The best process design is a matter of chemical engineering optimization depending on contaminants stemming from the first and third steps and the optional fourth step and is depending on the catalyst and process design in the second step. Due to ongoing catalyst and process developments, this optimum might change over time.

Hydrogen from methane pyrolysis in the second step is preferably purified and conditioned for the first step. This can be done either within the pyrolysis in the second step or in the methanation in the first step depending on e.g. site conditions for space and availability of utilities. Typical purity of hydrogen for industrial processing is 99.9-99.99 vol %. Even higher purity is possible using existing technologies in gas purification like pressure swing adsorption and membrane technologies and can be considered to optimize the circular carbon process.

Carbon monoxide for methanation stems from the third step. The reactions in the third step generate carbon monoxides. The carbon monoxide stream to the methanation should predominately contain CO preferably >80, more preferably >90%, even more preferably >95 Vol.-%.

The presence of CH4 and H2O as reaction products of the methanation is tolerable, but not preferred e.g. not to increase reactor and other equipment sizes. Other acceptable impurities in this stream depend on the methanation catalyst and process design and on engineering optimization of the overall process. Preferred is halogens <0.1 vol-ppm, total sulfur <0.1 mg/Nm$^3$ and tar <5 mg/Nm$^3$. Purification and conditioning of the CO-stream can be done in the third step after or between the reactions, but they can be done in the first step before the methanation reaction as well depending on engineering considerations.

The oxygen content in the mixture of feed gases hydrogen and carbon monoxide to the methanation is preferably <1 vol-%, more preferred <1000 vol-ppm.

First Step:

In the first step, hydrogen and carbon monoxide are reacted to produce methane and water known as CO methanation reaction (see for example S. Rönsch et al.: Review on methanation—From fundamental to current projects. Fuel 166 (2016) 276-296, Müller et al, "Energiespeicherung mittels Methan and energietragenden Stoffen—ein thermodynamischer Vergleich", Chemie Ingenieur Technik 2011, 83, No. 11, 2002-2013), Industrial applications of methanation as a catalytic process exist in gas cleaning from CO e.g. in ammonia processes to avoid catalyst poisoning and for purification of hydrogen from CO. In addition, CO methanation has been developed and realized for methane production from synthesis gas.

Nickel on alumina catalyst is standard in methanation, preferably a honeycomb shaped catalyst. Depending on the technology, 1 to 6 reactors at 1 to 70 bar and 200 to 700° C. have been reported. The temperature range of between 200 and 550° C. is preferred, even more preferred between 350 and 450° C., in a pressure range of 5 to 60 bar, more preferred 10 to 45 bar.

The carbon monoxide raw material stream to the methanation can have different compositions from pure CO (industrial purity) to a mixture of CO and CO2. The hydrogen demand and the amount of water production are lower for CO than CO2. The ratio of CO and CO2 in the carbon oxide is a result of engineering optimization for the complete circular process taking the process performance into account, but in addition potentially existing installations, site and economic conditions. Typical CO/CO2 mixture contains 80 to 100 Vol.-% CO and 0 to 20 Vol.-% CO2, preferable 85 to 100 Vol.-% CO and 0 to 15 Vol.-% CO2, even more preferable 90 to 100 Vol.-% CO and 0 to 10 Vol.-% CO2 in particular 95 to 100 Vol.-% CO and 0 to 5 Vol.-% CO2.

The CO2 content in the product of the methanation process should be kept low, meaning preferably below 0.5 vol %, e.g. by a surplus of hydrogen, to avoid formation of large CO amount in the following methane pyrolysis since this would lead to high efforts for the gas recycle stream in methane pyrolysis and for hydrogen purification after the methane pyrolysis step.

The hydrogen needed for the first step is preferably produced in the second step. In addition, hydrogen can be preferably produced via the fourth step, optionally using in addition water from the second step as a raw material to achieve high circularity meaning that most of the material streams are used. In general, hydrogen for the first step can be produced by any method externally from the circular carbon process. For example, the hydrogen can be produced by steam reforming of natural gas and/or bio methane with or without carbon capture and storage or utilization, by water electrolysis, it can be a byproduct from other processes like coking coal production or steam cracking or from any other hydrogen production method and the combination of different methods, including intermediate storage in tanks. Hydrogen supply can also be realized from an external pipeline.

The overall CO2 emissions need to be taken into account since the present invention targets to prevent CO2 emissions despite the use of carbon material as reducing agent. As long as methanation and methane pyrolysis are involved to close the circular carbon process, hydrogen production can be designed based on cost and overall CO2 emissions.

Purification and conditioning from first step to second step:

Technology for purification and conditioning of the gaseous products from the methanation is well known in the art, e.g. U.S. Pat. No. 8,568,512, F. G. Kerry: Industrial Gas Handbook: Gas Separation and Purification or https://biogas.fnr.de/gewinnung/anlagentechnik/biogasaufbereitung/. Typically, the following processes are used for methane purification: amine washing, pressurized water washing, pressure swing adsorption, physical adsorption, membrane processes and cryogenic processes. The second product water would be purified using standard methods in chemical engineering as well like extraction, membrane processes, adsorption and ion exchange.

Conditions for use of methane from the first step in second step are: preferably rest H2 up to 90 vol %, CO+CO2 preferably <0.5 vol %, total sulfur preferably <6 mg/m$^3$ as in typical natural gas, temperature preferably <400° C. to prevent start of pyrolysis before the second step, pressure reduction down to the pressure in the pyrolysis step, currently 1-5 bar, preferably 1-10 bar, is expected in the pyrolysis step, in later development steps, higher pressure in the second step will be achieved and preferably the first and the second steps can have similar pressure level of 5-30 bar plus/minus 1-2 bar to transfer methane from the first step to second step and/or hydrogen from the second step to the first step with only small pressure change.

Water for use in the optional fourth step or other external processes: Water as a raw material for industrial processes like electrolysis or steam methane reforming is typically used as demineralized water with a conductivity preferably <5*10-6 S/cm. Additional specifications are e.g. preferably <0.3 ppm SiO2 and CaCO3 preferably <1 ppm (Final Report BMBF funded project: "Studie Ober die Planung einer Demonstrationsanlage zur Wasserstoff-Kraftstoffgewinnung durch Elektrolyse mit Zwischenspeicherung in Salzkavernen unter Druck PlanDelyKaD". DLR et al., Christoph Noack et al, Stuttgart May 2, 2015). Specifications for water are also provided in ISO 3696 (1987) or ASTM (D1193-91).

Second Step:

In the second step, methane from the first step is decomposed into solid carbon and hydrogen. The process of methane decomposition is also referred to as methane pyrolysis since no oxygen is involved. The decomposition can be conducted in different ways known to the persons skilled in the art: catalytically or thermally, and with heat input via plasma, resistance heating, liquid metal processes or autothermal (see for example N. Muradov and T. Veziroglu: "Green" path from fossil-based to hydrogen economy: An overview of carbon-neutral technologies", International Journal Hydrogen Energy 33 (2008) 6804-6839, H. F. Abbas and W. M. A. Wan Daud: Hydrogen production by methane decomposition: A review, International Journal Hydrogen Energy 35 (2010) 1160-1190), R. Dagle et al.: An Overview of Natural Gas Conversion Technolgies for Co-Production of Hydrogen and Value-Added Solid Carbon Products, Report by Argonne National Laboratory and Pacific Northwest National Laboratory (ANL-17/11, PNNL26726) November 2017).

In case of autothermal methane pyrolysis, oxygen is introduced into the reaction for a partial combustion of methane and hydrogen for heat generation. In this case, the reactor effluent will become a synthesis gas and contain CO and CO2. This gas can be used internally or externally of the circular carbon process, or gases can be separated and H2 and CO2 are used e.g. in the first step, and CO in third step.

The pyrolysis reactor may operate at 500 to 2000° C. dependent on the presence of any catalyst (preferably 500 to 1000° C.) or without a catalyst (preferably 1000 to 2000° C.). The thermal decomposition reaction is preferably conducted in a pressure range from atmospheric pressure to 30 bar. The pressure range of between 5 and 10 bar is strongly preferred to deliver hydrogen to the methanation step without further pressure change.

Higher pyrolysis pressure than required for the first step might be relevant in case hydrogen from the second step is to be exported to a process external of the circular carbon process. In such case, the exported amount of hydrogen is preferably supplied by the optional fourth step with low carbon footprint.

If needed, additional methane from an external source can be fed into the reactor of the methane pyrolysis. Biomethane is a preferred external source. The amount of CO2 in the feedstock gas from the methanation process should be low in oxygen containing compounds to limit the amount of recycle gas within the process, which would lead to higher cost for operation of the recycle gas compressor.

The carbon type generated in the methane decomposition depends on the reaction conditions, reactor and heating technology. Example products are

- carbon black from plasma processes
- carbon powder from liquid metal processes
- granular carbon from thermal decomposition in fixed, moving or fluidized bed reactors.

Applications for carbon products from methane decomposition are discussed e.g. for aluminum and steel production, tire manufacturing, electrode manufacturing, polymer blending, additive for construction materials, carbon devices like heat exchangers, soil conditioning, or even storage.

Conditioning from Second Step to Third Step:

The carbon from the second step depends on selection of methane pyrolysis process technology and can e.g. be carbon black, pulverized or granular carbon. The form of the carbon containing material required for the third step depends on the reduction process and can be e.g. an electrode, coke, or particles. Typically mixing and solids processing or electrode forming are used to generate e.g. a Soderberg-Electrode for the aluminum reduction process.

Hydrogen from the second step is preferably used in the first step and is required at a pressure slightly above the pressure of the methanation reactor, i.e. 5-10 bar and at industrial purity. See above for further description.

Third Step:

In the third step, a chemical reaction is conducted whereas carbon is used in a carbon-containing material as a reducing agent, e.g. as a carbon-containing anode. In minor amounts carbon is used as a raw material to generate carbon monoxide CO, which is used as the reducing agent, or CO2 from the reduction process is converted with additional carbon to form CO, which is used as a reducing agent. The third step is using the carbon produced in the second step.

The third step preferably includes processes to modify and blend the carbon (carbon modification processes) from the second step with other forms of carbon or additional substances to be suitable for the use as a reduction agent in the third step. Typical carbon modification and blending processes are electrode production or in minor amounts the generation of carbon monoxide CO. The carbon modification processes can as well be part of the second step or might be viewed as separate step between the second step and the third step.

The following processes are preferred: a reduction of calcium oxide to calcium carbide via oxidizing carbon to carbon monoxide, a reduction of silicon oxide to silicon or silicon carbide via oxidizing carbon to carbon monoxide, a reduction of tin oxide to tin via oxidizing carbon to carbon monoxide, a reduction of chromium oxide to chromium via oxidizing carbon to carbon monoxide, a reduction of manganese oxide to manganese via oxidizing carbon to carbon monoxide and/or a reduction of calcium phosphate to phosphorus via oxidizing carbon to carbon monoxide.

For the preferred processes, the following table provides information on the main reducing agent according to the overall reaction, how carbon is applied to the reaction and about the main carbon oxide product. However, the processes are complex and can involve e.g. several stages and many processing units, so that carbon can be applied in different forms like electrodes and pulverized carbon or coke or similar forms.

TABLE 1

| Preferred processes for the third step involving a carbon containing raw material as a reducing agent | | | | |
|---|---|---|---|---|
| Product | Overall reaction | Reducing agent | Application form of reducing agent | Main carbon oxide formed |
| Calcium carbide | $CaO + 3 C \rightarrow CaC_2 + CO$ | C | electrode | CO |
| Silicon carbide | $SiO_2 + 3C \rightarrow SiC + 2 CO$ | C | powder | CO |
| Silicon | $SiO_2 + 2 C \rightarrow Si + 2 CO$ | C | electrodes | CO |
| Tin | $SnO_2 + 2 C \rightarrow Sn + 2 CO$ | C | In shaft reactor | CO |
| Chromium | $Cr_2O_3 + 3 C \rightarrow 2 Cr + 3 CO$ | C | briquettes | CO |
| Manganese oxide | $MnO_2 + C \rightarrow MnO + CO$ | C | In shaft/drum reactors | CO |
| Phosphorus | $2 Ca_3(PO_4)_2 + 6 SiO_2 + 10 C \rightarrow P_4 + 10 CO + 6 CaSiO_3$ | C | electrodes | CO |

Carbon sources for today's processes are petroleum cokes from refining operations, coal tar and coke from coal coking plants, or carbon from mining like graphite.

The carbon can be used in two functions: directly as a reducing agent or as a source for carbon monoxide, which is then used as a reducing agent. Both functions can be present in the third step and the reaction product can be mainly CO or $CO_2$ or a mixture of the two. In addition to the function of a reducing agent, CO can e.g. be used in combustion processes and generate heat for power and steam production. This use is assumed to be part of the third step although it can as well be located in the first and/or second steps or externally. CO can also be used as a reduction agent in a parallel process.

The carbon oxide generated in the third step is preferably separated from the process effluents. The effluents can have different composition of the main components CO and $CO_2$ including their mixtures accompanied by other substances like inerts, by-products from the process or contaminants. A preferred methods for separation of the carbon oxide are is separation of substances other than carbon oxide from the gas streams to generate a stream of $CO/CO_2$ as feed stream for the first step. Gas purification methods like absorption, adsorption, membrane technology can be applied here as well depending on the type and content of substances to be separated.

Conditioning from First Step to Fourth Step:

See above for water purification and conditioning before the optional fourth step or for other processes external from the circular carbon process.

Optional Fourth Step:

The fourth step includes a process of generating hydrogen, preferably a process of generating hydrogen with a Carbon Footprint of <1 kg $CO_2$/kg, system boundaries from raw materials to hydrogen inlet into the first step, $H_2$ to achieve high $CO_2$ emission reduction, see example for aluminum production. There are many ways in which this can be achieved, for example water electrolysis with electricity from renewable resources, standard steam reforming with carbon dioxide capture, standard steam reforming with biomethane at low carbon footprint of biomethane production, methane pyrolysis (see for example Compendium of Hydrogen Energy Vol. 1: Hydrogen Production and Purification. Edited by V. Subramani, A. Basile, T. N. Veziroglu. Woodhead Cambridge 2015). One preferred way is the water electrolysis separating electrically water into hydrogen and oxygen. Another preferred way is methane pyrolysis with natural gas with low carbon footprint or any of the processes combined with Carbon Capture and Storage.

If an electrolysis is used, preferably, the water produced in the first step is used in the fourth step to achieve high circularity of the overall process. Water electrolysis can be done with different technologies like alkaline, polymer electrolyte membrane (PEM) or as solid oxide electrolysis cell (SOEC). Typical parameters are described e.g. in (Final Report BM BF funded project: "Studie Ober die Planung einer Demonstrationsanlage zur Wasserstoff-Kraftstoffgewinnung durch Elektrolyse mit Zwischenspeicherung in Salzkavernen unter Druck PlanDelyKaD". DLR et al., Christoph Noack et al, Stuttgart May 2, 2015).

Joint Plant for Circular Carbon Process:

In addition, the present invention relates to a Circular Carbon Process System, a joint plant, comprising:

(i) a plant using carbon and/or carbon-containing material as reduction agent in a chemical reactor including a CO separation and conditioning downstream of the chemical reactor (ii) a methanation plant downstream producing methane and water (iii) a pyrolysis plant downstream of the methanation plant decomposing methane to solid carbon and hydrogen.

Optionally, the joint plant can include one or more of the following devices/plants:

plant producing hydrogen, preferably water electrolysis plant

For the connection of the different steps, the following considerations apply:

a gas pipeline feeding methane-rich mixture from the first step to the second step a carbon solids transport device between the second step and the third step a gas pipeline for carbon oxide transport from the third step to the first step a gas pipeline for hydrogen transport from the second step and/or the fourth step to the first step a pipeline for liquid water transport from the first step to the fourth step a gas pipeline for hydrogen supply from external production to the first and/or third steps a gas pipeline for $CH_4$ and other light hydrocarbons supply from external production to the second and/or third steps a gas/liquid pipeline for $CO/CO_2$ supply from external production to the first step a gas pipeline for CO supply from external production to the third step a transport pipeline or solids transport device for C supply from external sources to the third step any other supply options like hydrogen in bundles of bottles including intermediate storage in tanks The different reactors can be connected by a skilled person in the art taking the needed gas conditions and purities for each step into account. The benefit of the joint plant set-up still exists if the plants are located in a radius about 50 to 100 km.

Advantages of the circular carbon process are

Avoidance of $CO_2$ emissions to enable carbon neutral production while still using carbon containing material as a reduction agent Reducing of hydrogen and electricity demand by using CO methanation instead of CO2 methanation Generation of a homogeneous carbon material without significant changes in purity of other material properties Replacement of carbon purchases by own production Investment alternative for CO2 emission reduction versus Carbon Capture and Storage (CCS). CCS would require CO2 capture with energy demand. This energy demand can be fulfilled by reaction heat from the exothermic methanation reaction.

DETAILED DESCRIPTION OF THE FIGURE

The FIGURE is a schematic diagram of the circular carbon process reacting carbon monoxide and hydrogen to generate methane as a feed to methane pyrolysis to generate carbon for the process using carbon as reducing agent, hydrogen from methane pyrolysis can be used in the methanation process and/or hydrogen can be supplied by an optional fourth step.

The invention claimed is:

1. A circular carbon process, comprising:

a) reacting hydrogen and carbon monoxide to produce methane and water, b) decomposing the methane into carbon and hydrogen, and c) producing carbon monoxide and a reduced substance in a chemical process, wherein the carbon is used as reducing agent and/or the carbon is used in a carbon-containing material as reducing agent, the methane produced in a) is used in b), wherein the carbon produced in b) is used in c), and wherein the carbon monoxide produced in the c) is used in a), a) and b) are both conducted in a pressure range from 1 to 30 bar, and a) comprises a purification and conditioning of a gaseous product from said reacting to result in a CO and CO2 content of <0.5 vol %.

2. The process according to claim 1, wherein the chemical process in c) is a reduction of calcium oxide to calcium carbide via oxidizing of carbon to carbon monoxide, a reduction of silicon oxide to silicon or silicon carbide via oxidizing of carbon to carbon monoxide, a reduction of tin oxide to tin via oxidizing of carbon to carbon monoxide, a reduction of chromium oxide to chromium via oxidizing of carbon to carbon monoxide, a reduction of manganese oxide to manganese via oxidizing of carbon to carbon monoxide, and/or a reduction of calcium phosphate to phosphorus via oxidizing of carbon to carbon monoxide.

3. The process according to claim 1, wherein reaction heat from an exothermic methanation reaction in a) is used in c) for separation or purification of the carbon monoxide.

4. The process according to claim 1, wherein the hydrogen produced in b) is used in a).

5. The process according to claim 1, further comprising:

d) producing hydrogen, which is used in a).

6. The process according to claim 5, wherein the hydrogen is produced via water electrolysis or steam methane reforming with or without carbon capture and storage in d).

7. The process according to claim 6, wherein the water produced in a) is used for the water electrolysis in d).

8. The process according to claim 1, wherein at least one stream from outside the circular process comprising $H_2$, $CH_4$, CO, $CO_2$ and/or C is introduced into the circular process, or wherein at least one stream comprising $H_2$, $CH_4$, CO, $CO_2$ and/or C is extracted from the circular process to supply external demand and/or for storage of carbon.

9. The process according to claim 8, wherein biogas is used as an additional methane source.

10. The process according to claim 1, wherein hydrogen and carbon monoxide are reacted to produce methane and water by a surplus of hydrogen.

11. The process according to claim 1, wherein amine washing, pressurized water washing, pressure swing adsorption, physical adsorption, membrane processes or cryogenic processes are used for the purification and conditioning of the gaseous product.

12. The process according to claim 1, wherein step c) includes an electrode production process by modifying and blending the carbon from step b) with at least one other form of carbon or an additional substance.

* * * * *